(12) United States Patent
Hohmann

(10) Patent No.: US 12,187,833 B2
(45) Date of Patent: Jan. 7, 2025

(54) RADIATION-CURABLE COMPOSITION FOR USE IN RAPID PROTOTYPING OR RAPID MANUFACTURING METHODS

(71) Applicant: KULZER GMBH, Hanau (DE)

(72) Inventor: Alfred Hohmann, Schmitten (DE)

(73) Assignee: Kulzer GmbH, Hanau (DE)

( * ) Notice: Subject to any disclaimer, the term of this patent is extended or adjusted under 35 U.S.C. 154(b) by 652 days.

(21) Appl. No.: 17/437,278

(22) PCT Filed: Mar. 10, 2020

(86) PCT No.: PCT/EP2020/056354
§ 371 (c)(1),
(2) Date: Sep. 8, 2021

(87) PCT Pub. No.: WO2020/182814
PCT Pub. Date: Sep. 17, 2020

(65) Prior Publication Data
US 2022/0162370 A1 May 26, 2022

(30) Foreign Application Priority Data

Mar. 11, 2019 (DE) .................. 10 2019 106 151.2

(51) Int. Cl.
| | |
|---|---|
| *C08F 2/50* | (2006.01) |
| *B33Y 70/00* | (2020.01) |
| *B33Y 80/00* | (2015.01) |
| *C08F 290/06* | (2006.01) |
| *B33Y 10/00* | (2015.01) |

(52) U.S. Cl.
CPC .......... *C08F 290/067* (2013.01); *B33Y 70/00* (2014.12); *B33Y 80/00* (2014.12); *C08F 2/50* (2013.01); *B33Y 10/00* (2014.12)

(58) Field of Classification Search
CPC ............ C08F 2/50; B33Y 70/00; B33Y 80/00
USPC ....................................................... 523/109
See application file for complete search history.

(56) References Cited

U.S. PATENT DOCUMENTS

| | | | |
|---|---|---|---|
| 2010/0104765 A1* | 4/2010 | Yamashina | ........ C08G 18/8125 427/520 |
| 2014/0131908 A1 | 5/2014 | Sun et al. | |
| 2014/0239527 A1* | 8/2014 | Lee | ........................ B29C 64/106 264/17 |
| 2016/0332367 A1 | 11/2016 | Sun et al. | |

FOREIGN PATENT DOCUMENTS

| | | |
|---|---|---|
| EP | 3 632 995 A1 | 9/2019 |
| EP | 2 986 654 B1 | 3/2020 |
| WO | 01/30306 A1 | 5/2001 |
| WO | 2014/098956 A1 | 6/2014 |
| WO | 2014/172716 A1 | 10/2014 |

* cited by examiner

*Primary Examiner* — Deve V Hall
(74) *Attorney, Agent, or Firm* — Norris McLaughlin, P.A.

(57) ABSTRACT

A polymerisable radiation-curable, in particular UV-Vis-, UV- or Vis-curable, composition comprising:
(i) monomers, wherein the monomers comprise:
(a.1) at least one triacrylate derived from 1,3,5-tris(ω-hydroxyalkyl) isocyanurate, wherein the hydroxyalkyl residue comprises 1 to 8 C-atoms and may be linear, branched and/or cyclic, and
(a.2) at least one di-functional monomer, not being a urethane (meth)acrylate, and
(ii) at least one further component, comprising:
at least one photo-initiator for the UV and/or Vis spectral region or a photo-initiator system for the UV and/or Vis spectral region. Also disclosed is a blank in the form of a three-dimensional moulded body of a polymerised composition, in particular of a radiation-cured composition for producing dental prosthetic parts, orthopaedic appliances or dental pre-forms, and also to the use of the composition for producing dental prosthetic parts, orthopaedic appliances or dental pre-forms in a rapid prototyping or in a rapid manufacturing or rapid tooling method.

13 Claims, No Drawings

RADIATION-CURABLE COMPOSITION FOR USE IN RAPID PROTOTYPING OR RAPID MANUFACTURING METHODS

This application is a 371 of PCT/EP2020/056354, filed Mar. 10, 2020, which claims foreign priority benefit under 35 U.S.C. § 119 of the German Patent Application No. 10 2019 106 151.2, filed Mar. 11, 2019, the disclosures of which are incorporated herein by reference.

The invention relates to a polymerisable radiation-curable, in particular UV-Vis-, UV- or Vis-curable, composition comprising
- (i) monomers, wherein the monomers comprise
  - (a.1) at least one triacrylate derived from 1,3,5-tris($\omega$-hydroxyalkyl) isocyanurate, in particular from 1,3,5-tris(2-hydroxylalkyl) isocyanurate, wherein the hydroxyalkyl residue comprises 1 to 8 C-atoms and may be linear, branched and/or cyclic, and
  - (a.2) at least one di-functional monomer, not being a urethane (meth)acrylate, and
- (ii) at least one further component, comprising
  at least one photo-initiator for the UV and/or Vis spectral region or a photo-initiator system for the UV and/or Vis spectral region and optionally at least one stabiliser. Moreover, the invention relates to a blank in the form of a three-dimensional moulded body of a polymerised composition, in particular of a radiation-cured composition for producing dental prosthetic parts, orthopaedic appliances or dental pre-forms, and also to use of the composition for producing dental prosthetic parts, orthopaedic appliances or dental pre-forms in a rapid prototyping or in a rapid manufacturing or rapid tooling method.

Digital manufacturing methods such as subtractive or additive processes (material build-up processes) are becoming increasingly important in dental field in addition to manual manufacturing methods. The advantage of additive processes is saving of expensive raw materials and faster production of the objects. Generative methods are already known in dental field e.g. in the form of laser sintering from CoCr, Ti or polymers for producing crowns and bridges, implant components or models.

Compositions of acrylates or derivatives of acrylates for producing dental restorations having an appropriate characteristics profile in respect of the mechanical requirements in dental field according to DIN EN ISO 207952 are not obtainable up to now (see Quintessenz Zahntech. 2017-43 (10): page 1325). There is thus a general need for materials for producing anatomical models, anatomical table-top models and in particular for producing anatomical models as substitute of the dental plaster model of the dentition, being produced from the impression of the dental situation and the gingiva or the dentition, respectively, of a patient, or for producing prosthetic parts or definitive dental restorations. Furthermore, there is thus a need for compositions for producing definitive prosthetic parts, orthopaedic appliances or dental pre-forms.

The impression and the model, here also referred to as anatomical model or working model form the basis for custom-fit prosthetic restorations. Only if dentist and dental technician adhere to the material-specific requirements during impression taking and model production you will receive an individualised optimal restoration.

Usually, the dental technician uses plaster for model production. It is easy to use and meets the requirements of precise, dimensionally stable, surface-smooth models. The requirements for dental anatomical plaster models are given below: volume stability, lowest expansion, no contraction, storage stability, compatible with disinfectants, insulating agents and waxes, a smooth and non-porous surface, sufficient pressure resistance, high edge stability, good abrasion resistance, high thermal capacity, in particular in case of wax extraction, in conjunction with or without water.

It was the object of the present invention to provide a composition having good radiation-curable properties, in particular UV and/or Vis radiation-curable properties, with good polymerisation depth in radiation curing. Moreover, the radiation-cured compositions should have good mechanical properties at both ambient room temperature and also elevated temperature, in order to be used in the production of anatomical models. The compositions should thus meet the requirement of model materials, for producing models for model casting, implantology, saw cut, and master models, as well as precise counter-bite models. Therefore, it was the object to provide radiation curable compositions, usable in additive/generative processes, that, as a printed moulded body in cured state, meet the following requirements: Maintaining the mechanical properties and dimensional stability at temperatures of 45° C. to 55° C. in the pressure pot, dimensional stability in thermoforming process, as well as also in cleaning e.g. using a steam jet device, storage stability of the light-curing composition without significant viscosity changes over the storage period, sufficient reactivity when being irradiated using laser, LED or DLP projector, work pieces/moulded bodies being printable with sufficient geometrical precision/resolution, colour stability of the mixture, and no or only a few thixotropy. It was thus the object of the invention to provide a radiation-curable composition, having, when being tested in water at 55° C. in polymerised state, a flexural strength of at least 40 MPa and a flexural modulus of at least 800 MPa.

Further requirements for a dental plaster model in several working steps are outlined below: model in conjunction with thermal impacts and water: Casting-on of plastic saddle in model casting (20 min. at 55° C. in a water bath), completing a partial prosthesis/model casting (20-30 min. at 55° C. in a water bath), completing a total prosthesis (injection technique Palajet/cuvette technique—30 min. at 55° C. in a water bath), completing a total prosthesis tamping-pressing technique (30-40 min. at 100° C. in a water bath), thermoforming trays (20-30 min. at 55° C.), water vapour for cleaning (70° C.-110° C.), extracting (3-5 min. at 80° C.-100° C.), veneering with Pala Veneers (55° C., 2 bar, 20 min.).

Model in conjunction with insulations and mechanical impacts: in-articulating, i.e. the model is mechanically loaded in an articulator, insulation against prosthesis plastic, insulation against veneering composite, insulation against wax, out-blockability with UV plastic and/or waxes, dipping wax.

Model in conjunction with thermal impacts without water: thermoforming (155-170° C./1 to 2 minutes), hot glue gun to fix the models, gluing wax to fix the models, out-blockability with UV plastic and/or wax, dipping wax, thermoforming foil and manual curing of composites in HiLite Power/3D (twice 90 sec. each and once 180 sec.), curing of occlusal splints in HiLite Power/3D (twice 5 min. each), milling stump for milling technique (temperature-resistant against accumulated heat).

Behaviour of the polymerised composition in other working steps: dimensionally stable and good cleaning properties in an ultrasonic bath with isopropanol, discoloration and cleaning in case of articulation foil (Bausch, red, blue, black), discoloration and cleaning in case of occlusion spray (several manufacturers), abrasion resistance at the preparation margin (crowns, bridges, model casting clamping teeth), break/abrasion resistant (in the articulator—plaster against plastic; plastic against plastic).

Situation models and all working models are the basis for all further dental technical work. In order to meet high aesthetic requirements, resin compositions for definitive dental restorations, such as e.g. work models, orthodontic models must have dimensional stability and thermal stability. If one wants to replace plaster models with printed plastic models in order to obtain the advantages of the digital workflow, the plastic models must have the same positive properties as plasters. However, due to various physical and chemical boundary conditions, plastics are subject to thermal plasticity, which must be kept within limits by an optimal selection of the monomers.

So far, there are no materials having all thermostable properties mentioned, so they can only be used for some dental applications.

Therefore, it was also an object of the invention to provide a composition comprising monomers having a particularly high thermal stability and dimensional stability, to resist the elevated temperatures when using the polymerised composition as moulded part in a pressure pot as well as in case of thermoforming of occlusal splints. During the production of aligners, the elevated temperatures must be resisted several times.

The objects of the invention are solved by the composition according to claim 1 as well as the polymerised composition according to claim 11, and also the blank according to claim 12 and the use according to claim 13. Preferred embodiments are disclosed in the dependent claims and in detail in the description.

Subject matter of the invention are polymerised compositions, in particular radiation-curable compositions, preferably polymerisable by means of UV-Vis, UV or Vis radiation, comprising
- (i) monomers and
- (ii) at least one further component, wherein (i) the monomers comprise
  - (a.1) at least one triacrylate derived from 1,3,5-tris(ω-hydroxyalkyl) isocyanurate, wherein the hydroxyalkyl residue each independently comprises 1 to 8 C-atoms, and in particular is linear, branched and/or cyclic with 3 to 8 C-atoms, preferred is a hydroxyalkyl residue having 1 to 6 C-atoms, particularly preferably having 1 to 4 C-atoms, preferably having 1 to 3 C-atoms, particularly preferred is hydroxyethyl, and
  - (a.2) at least one di-functional monomer, not being a urethane acrylate or urethane methacrylate, and (ii) the at least one further component comprises at least one photo-initiator for the UV- and/or Vis spectral region or a photo-initiator system for the UV and/or Vis spectral region, as well as optionally at least one stabiliser, and optionally further usual additives, optionally pigment(s) or dye(s).

Particularly preferred compositions have a viscosity at ambient room temperature (approx. 20° C. to 23° C.) of less than or equal to 5000 m·Pas, preferably of less than or equal to 3000 m·Pas, particularly preferably of 500 to less than 2500 m·Pas.

According to an embodiment, preferred monomers comprise (a.1) at least one triacrylate derived from 1,3,5-tris(ω-hydroxyalkyl) isocyanurate, particularly preferred are 1,3,5-tris(2-hydroxyethyl) isocyanurate triacrylate, 1,3,5-tris(2-hydroxymethyl) isocyanurate triacrylate, 1,3,5-tris(2-hydroxyethyl) isocyanurate trimethacrylate, 1,3,5-tris(2-hydroxymethyl) isocyanurate trimethacrylate or mixtures containing at least two of the monomers.

Further preferred (i) monomers are selected from: (a.2) at least one di-functional monomer, not being a urethane (meth)acrylate, comprising (b) and/or (c), with
- (b) di-functional acrylates having a bivalent alicyclic group and di-functional methacrylates having a bivalent alicyclic group, and optionally
- (c) at least one disubstituted 4,4'-di(oxabenzol) dialkyl methane of formula I

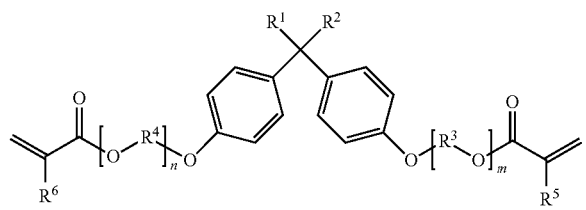

with $R^1$, $R^2$, $R^5$ and $R^6$ each independently selected from H or C1 to C4-alkyl, and with $R^3$ and $R^4$ each bivalent C1 to C4-alkylene, with n=0 to 6 and m=0 to 6, and optionally
- (i) the monomers comprise
- (d) at least one at least di-functional urethane (meth) acrylate,
- (e) at least one mono-functional acrylate having an alicyclic group and/or mono-functional methacrylate having an alicyclic group.

Preferred are disubstituted 4,4'-di(oxabenzol) dialkyl methanes of formula I with $R^1$ and $R^2$ each methyl, and $R^5$ and $R^6$ the same and selected from H, methyl and ethyl, in particular with $R^5$ and $R^6$ the same and selected from H and methyl, and with $R^3$ and $R^4$ each independently bivalent ethylene or propylene with n=1 to 6, preferably n=2 to 4, and with m=1 to 6, preferably m=2 to 4, preferably with n=2 and m=2 or with n=4 and m=4 as well as mixtures thereof.

In preferred alternatives, $R^1$ and $R^2$ in formula I may be methyl each, and $R^5$ and $R^6$ may be the same and selected from H, methyl and ethyl, preferably $R^5$ and $R^6$ are the same and selected from H and methyl, and with $R^3$ and $R^4$ each independently bivalent ethylene or propylene with n=1 to 6, wherein preferably n=2 to 4, and with m=1 to 6, particularly preferably n=2 to 4 and m=2 to 4, more preferably with n=2 and m=2 or with n=4 and m=4 as well as mixtures thereof. Particularly preferred is a mixture of 4,4'-di(oxabenzene) dialkyl methane of formula I a) with $R^1$ and $R^2$ each methyl, and $R^5$ and $R^6$ equal to H and with $R^3$ and $R^4$ each independently bivalent ethylene with n=1 to 6, preferably n=2 to 4, and with m=1 to 6, preferably m=2 to 4, preferably with n=4 and m=4 as well as mixtures thereof in mixtures with b) with $R^1$ and $R^2$ each methyl, and $R^5$ and $R^6$ equal to methyl and with $R^3$ and $R^4$ each independently bivalent ethylene with n=1 to 6, preferably n=2 to 4, and with m=1 to 6, preferably m=2 to 4, preferably with n=2 and m=2 as well as mixtures thereof.

A preferred at least di-functional monomer, not being a urethane (meth)acrylate, is selected from (b) di-functional acrylates having a bivalent alicyclic group and di-functional methacrylates having a bivalent alicyclic group. Particularly preferred (b) they are selected from tricyclodecane dimethanol diacrylate (TCDDA), tricyclodecane dimethanol dimethacrylate, tricyclodecane diethanol diacrylate, tricyclodecane diethanol dimethacrylate and/or mixtures thereof (partially synonymous to bis(methacryloyloxymethyl) tetrahydrodicyclopentadiene or bis(acryloyloxymethyl) tetrahydrodicyclopentadiene.

Preferably, all monomers (a), (b), (c), (d), (e) and (f) according to the invention have an average molecular weight (weight average) of less than 2000 g/mol, particularly preferably the monomers (a), (b), (d), (e) and (f) have an average molecular weight of less than 1000 g/mol.

Semi-crystalline plastics (many usual plastics have a crystalline part of 10 to 80%) possess both a glass-transition temperature, the amorphous phase freezes below which (along with embrittlement), and a melting temperature, the crystalline phase dissipates at which. Glass-transition is not a $1^{st}$ order phase transition and is thus not linked to an exact temperature as the melting point in case of crystals. The found value systematically varies depending on the time and length scale or movement mode of the molecular dynamics the measurement method used (see below) being sensitive to. Whether a plastic can be used above or below its glass-transition temperature depends on the type of plastic (it is to be noted that the glass-transition temperature of a plastic increases with its cross-linking density, i.e. the glass-transition temperature of a thermosetting plastic is significantly higher than that of a thermoplastic).

It is also important for the selection of monomers that they interconnect well with the filler optionally used. Usually, polyurethanes, acrylates, polyesters and other monomers do not take a good bond with the fillers used. Therefore, the fillers are usually silanised or hydrophobized at the surfaces to improve bonding with the monomers.

If no inorganic fillers may be used in the polymerisable composition due to the specific dental application, e.g. due to the viscosity aimed of the composition, there is the possibility to use dyes or pigments in the composition for reflection of the irradiation, in particular diffuse reflection or scattering respectively of the incoming irradiation. Dyes are considered as compounds being soluble in the polymerisable composition and preferably form a clear solution.

The radiation-curable compositions according to the invention may preferably be irradiated using a radiation source emitting light in the Vis spectral region, particularly preferred are radiation sources emitting irradiation from 360 to 750 nm, in particular at approx. 385 nm, particularly preferably at approx. 405 nm. Particularly preferably, the composition according to the invention may be irradiated using a polychromatic radiation source, such as a DLP projector, or preferably using a monochromatic radiation source, such as a laser projector, in the Vis spectral region from 380 to 660 nm.

The content of photoinitiator may be reduced in the composition when the said pigments and/or dyes being added. A content of photoinitiator being too high may result in a so-called "overcuring" of the irradiated composition, inaccuracies and/or geometry changes, so that the dental parts produced appropriately are not usable.

Use of the optionally usable inorganic fillers, pigments or dyes according to the invention leads to even scattering of the radiation source, in particular of the UV and Vis radiation source, in the monomer matrix of the composition, so that an even curing of the composition is anticipated. Ultimately, the polymerised compositions have higher values of fracture work achieved.

The composition according to the invention has the following properties a) a flexural strength of greater than or equal to 40 MPa, in particular greater than or equal to 75 MPa and/or b) an E-modulus of greater than or equal to 800 MPa, in particular greater than 1500 MPa, in particular greater than or equal to 2000 MPa following DIN EN ISO 20795-2, in particular usually at ambient room temperature, preferably 23° C. plus/minus 2° C., preferably from ambient room temperature to (in water) 55° C. after irradiation using a radiation source in the Vis spectral region, in particular from 385 to 405 nm, preferably after irradiation in a stereolithography method and obtaining a polymerised composition, preferably in the form of a blank, 3D moulded part, dental prosthetic part, anatomical model, anatomical tabletop model, dental working model, dental full model, dental die model, anatomical or dental saw-cut model, in particular situation model, counter-bite model, functional model, Pre-model, repair model, precision model, master model as well as precise counter-bite model, anatomical models for replacement of the dental plaster model of the dentition, prosthetic parts, orthopaedic appliances or dental pre-forms, as well as optional post-tempering of the polymerised composition using a radiation source. Preferably, the radiation-cured composition, in particular as moulded body or blank, has the flexural strengths and or E-moduli described below. For definition of the above dental models see Lehrbuch der Zahntechnik, Band 3, Quintessenz Verlag, A. Hohmann, W. Hielscher, 5. Aufl., 2012. Post-curing or post-tempering, respectively may preferably be carried out e.g. using a laboratory light device (HiLite Power 3D) or in the light furnace preferably with a light spectrum of 390-540 nm.

Optionally, the composition may additionally contain as (a.2) at least one di-functional monomer, not being a urethane acrylate or urethane methacrylate, at least one polyether diacrylate, such as poly(ethylene glycol) diacrylate, poly(ethylene glycol) di(alkyl) acrylate, poly(propylene glycol) diacrylate, poly(propylene glycol) di(alkyl) acrylate or a mixture of at least two of the afore-mentioned monomers. Preferred polyether diacrylates may be selected from triethylene glycol dimethacrylate, diethylene glycol dimethacrylate and/or tetraethylene glycol dimethacrylate. Alternatively or additionally, the composition may comprise diacrylates selected from diacrylates selected from decane diol di(meth)acrylate, dodecane diol di(meth)acrylate, hexyl decane diol di(meth)acrylate, butane diol di(meth)acrylate or mixtures containing at least one of the acrylates.

The indication in parentheses in the terms (methyl) acrylate or (alkyl) acrylate means that the acrylates may be present as acrylate or methyl acrylate as well as alternatively as alkyl acrylate.

Likewise, preferred monomers as at least one further monomer in the composition may be selected from:
(d) at least one at least di-functional urethane (meth) acrylate, and/or
(f) at least one mono-, tri-, tetra- or multi-functional monomer, in particular not being a urethane (meth) acrylate.

Hydroxyethyl acrylate may be used as mono-functional monomer. Likewise, hydroxypropyl acrylate, hydroxyethyl methacrylate, hydroxypropyl methacrylate and/or hydroxyethyl acrylate optionally as mixture of at least two of the afore-mentioned monomers may be used.

Furthermore, the composition may contain (d) at least one at least di-functional urethane (meth)acrylate, being selected from di-functional urethane (meth)acrylates having a bivalent alkylene group (di-functional urethane acrylates and/or di-functional urethane methacrylates).

The di-functional urethane (meth)acrylate having a bivalent alkylene group is preferably selected from linear or branched urethane dimethacrylates functionalised with a bivalent alkylene group, functionalised polyethers having alkylene group(s), such as bis(methacryloxy-2-ethoxycarbonylamino)alkylene, bis(methacryloxy-2-ethoxycarbonylamino)-substituted polyalkylene ethers, preferably 1,6-bis(methacryloxy-2-ethoxycarbonylamino)-2,4,4-trimethyl hexane, UDMA or HEMA-TDMI, respectively. Preferred is a bis(methacryloxy-2-ethoxycarbonylamino)alkylene, wherein alkylene comprises linear or branched C3 to C20, preferably C3 to C6, such as particularly preferably an alkylene substituted with methyl groups, such as HEMA-TDMI. The bivalent alkylene preferably comprises 2,2,4-trimethyl hexamethylene and/or 2,4,4-trimethyl hexamethylene.

The (f) tri-, tetra- or multi-functional monomers may be selected from:

Particularly preferably, from pentaerythritol tetraacrylate (TG 105° C.), ditrimethylolpropane tetraacrylate (TG 100° C.). Also suitable are trimethylolpropane triacrylate (TG 60° C.), dipentaerythritol pentaacrylate (TG 90° C.), ethoxylated (4)pentaerythritol tetraacrylate (TG 70° C.) and ethoxylated (4)pentaerythritol tetraacrylate (TG 70° C.). In addition, tri-functional monomers may be selected from, wherein the said are preferably used in the total composition with 0 to 10% by weight only, in particular with 0.01 to 5% by weight: ethoxylated (20)trimethylolpropane triacrylate (TG −40° C.), ethoxylated (3)trimethylolpropane triacrylate, propoxylated (3)trimethylolpropane triacrylate, ethoxylated (6)trimethylolpropane triacrylate (TG −10° C.), ethoxylated (9)trimethylolpropane triacrylate (TG −20° C.), propoxylated (3)glyceryl triacrylate (TG 20° C.), ethoxylated (15) trimethylolpropane triacrylate (TG −30° C.).

A TG is preferably determined by means of DSC. The glass-transition temperatures disclosed may be gathered from "polymer handbooks" known by the person skilled in the art, from information of the manufacturer of the monomers. Insofar as no information concerning glass-transition temperatures is available, the said may be determined by means of DSC, DMS (dynamic mechanical analysis), dielectric relaxation spectroscopy or dilatrometry. DSC measurement is a usual method for determination of the glass-transition temperature of the homopolymers. On that point, the homopolymer is dryed, heated to 120° C., rapidly cooled down to −100° C. and subsequently heated to 150° C. or higher up to 300° C. with 20° C./minute and the data of the glass-transition temperature are determined. The glass-transition temperature is measured as a mean. $1/Tg = w1/Tg_{(1)} + w2/Tg_{(2)}$ with w1 and w2 as mass proportion of the respective co-monomers and $Tg_{(1)}$ and $Tg_{(2)}$ for the respective glass-transition temperature of the homopolymers of monomers 1 and 2. In case of further co-monomers, further terms ($wn/Tg_{(n)}$) are integrated into the equation. The glass-transition temperature of co-polymers may be approximated by the Fox equation, see above and [Bulletin of the American Physical Society 1, 3 Page 123 (1956)]. TG(total) may be calculated by 1/TG(total) according to the following formula, wherein the monomers are present in the polymer in the total composition according to the following weight proportions (w1, w2, w3, w4, w5 and wn). $1/TG(total) = w1/TG_{(1)} + w2/TG_{(2)} + w3/TG_{(3)} + $ optionally $w4/TG_{(4)} + $ optionally $w5/TG_{(5)} + $ optionally $wn/TG_{(n)}$, with w1, w2, w3, w4, w5 and wn each weight proportion of the monomer in the total composition.

Optionally, one or more fillers may be contained in the composition, such as a doted silicon dioxide filler, in particular a mixed oxide of zirconium dioxide and silicon dioxide. Particularly preferred are i.a. agglomerated mixed oxides, comprising 75 to 99% by weight silicon dioxide and from 1 to 25% by weight zirconium dioxide, based on the total composition of the mixed oxide, in particular the mixed oxide comprises from 85 to 90% by weight silicon dioxide and 10 to 15% by weight zirconium dioxide, wherein it is further preferred for the primary particles of the agglomerated oxide particles to comprise microcrystalline domains of 4 to 7 nm and for the crystallinity index to be advantageously 0.6 to 0.7—determined according to the method of Windisch et al. (WO 01/30306A)—and for the agglomerated oxide particles to be surface-modified with an organofunctional silane being reactive with respect to at least one monomer and/or polymer component. Said agglomerated oxide particles treated according to the invention have outstanding properties in abrasion measurements, regarding the gloss level, an outstanding transparency and very good values in reflexion and roughness measurements after a toothbrush test.

The particle sizes of the inorganic fillers, such as of the at least one inorganic oxide, mixed oxide or dental glass, e.g. comprising barium aluminium oxide, have an average particle diameter of $d_{50}$ less than 10 μm for the present application, particularly preferably the fillers have a particle diameter of approximately 3 to 70 nm, in particular of 10 to 50 nm (nanometers), optionally the particles may be aggregated or agglomerated as particles with up to 10 μm. The primary particles sizes of the inorganic fillers, which may optionally be present as agglomerated and/or aggregated primary particles, have an average particle diameter of approximately 3 to 70 nm, in particular of 10 to 50 nm. Preferably, the mixed oxides of zirconium dioxide with silicon dioxide have a primary particle size of 3 to 70 nm. The advantage of the very small particle diameters, which may be aggregated and/or agglomerated as appropriate, is that the light is scattered in a substantially diffuse manner by these particles in case of radiation curing and thus leads to better curing in stereolithography methods or DLP methods.

Furthermore, it is preferred for the composition to be non-thixotropic. In addition, it is particularly preferred for the composition to have a viscosity of less than 3000 m·Pas, in particular from 500 to less than 2500 m·Pas, preferably from 500 to 2000 m·Pas, particularly preferably from 500 to 1600 m·Pas. The viscosity is preferably measured according to DIN 1342-2; 2003-11 Newtonian liquids or DIN 1342-3; 2003-11 non-Newtonian liquids using a rheometer (Anton Par, Physica MCR 301, viscosity ranges 200-3000 m·Pas at 100/s 23° C.). The compositions according to the invention have no or preferably only a low thixotropy. The compositions produced are structurally viscous, wherein it is preferred for the compositions to be structurally viscous with and without fillers. According to another embodiment, it is preferred if almost no changes in viscosity occur over a longer storage period. Furthermore, the compositions have a very good reactivity when being irradiated using a laser or DLP projector.

A preferred composition may further comprise as monomers:
(d) at least one di-functional urethane acrylate or urethane methacrylate selected from di-functional urethane acrylates having a bivalent alkylene group and urethane methacrylates having a bivalent alkylene group, and/or
(e) at least one mono-functional acrylate having an alicyclic group and/or mono-functional methacrylate having an alicyclic groups elected from (octahydro-4,7-methano-1H-indenyl) methanol acrylate, (synonymous to (octahydro-4,7-methano-1H-indenyl) methyl acrylate), (octahydro-4,7-methano-1H-indenyl) methanol methacrylate (TCDA), (octahydro-4,7-methano-1H-indenyl) ethanol acrylate and (octahydro-4,7-methano-1H-indenyl) ethanol methacrylate, and optionally
(f) at least one mono-, tri-, tetra- or multi-functional monomer, in particular not being a urethane (meth) acrylate. Alternatively, (i) the monomers may further comprise acrylic esters and/or methacrylic esters of polyethers selected from dimethacrylic esters of polyethers, tri-, tetra- or multi-functional methacrylic esters of polyethers, diacrylic esters of polyethers, tri-, tetra- and/or multi-functional acrylic esters of polyethers.

Preferred combinations of the afore-mentioned monomers are monomers selected from (d) in conjunction with monomers from (e) and optionally additional (f). The afore-mentioned acrylic esters of (octahydro-4,7-methano-1H-indenyl) alkanols may occur as isomers, so that any isomers may be used alone or in mixtures.

A particularly preferred composition comprises as (i) monomers
a) 5 to 45% by weight at least one triacrylate derived from 1,3,5-tris(ω-hydroxyalkyl) isocyanurate, wherein the hydroxyalkyl residue comprises 1 to 8 C-atoms, particularly preferred is hydroxyethyl, and
(b) 5 to 45% by weight at least one di-functional acrylate having a bivalent alicyclic group and/or di-functional methacrylate having a bivalent alicyclic group, and
(c) 0 to 60% by weight at least one disubstituted 4,4'-di (oxabenzol) dialkyl methane of formula I with $R^1$, $R^2$, $R^5$ and $R^6$ each independently selected from H or C1 to C4-alkyl, and with $R^3$ and $R^4$ each bivalent C1 to C4-alkylene, with n=0 to 6 and m=0 to 6, and optionally
(d) 0 to 60% by weight at least one at least di-functional urethane acrylate and/or di-functional urethane methacrylate,
(e) 0 to 20% by weight at least one mono-functional acrylate having an alicyclic group and/or mono-functional methacrylate having an alicyclic group, and
(ii) 0.01 to 5% by weight of the at least one further component comprising at least one photo-initiator for the UV and/or Vis spectral region or a photo-initiator system for the UV and/or Vis spectral region, and optionally at least one stabiliser for the UV- and/or Vis spectral region, and optionally at least one pigment and/or dye, as well as further usual additives, wherein the total composition amounts to 100% by weight.

According to a further embodiment, a composition is preferred, comprising
(i) monomers comprising
(a) 5 to 35% by weight at least one triacrylate derived from 1,3,5-tris(ω-hydroxyalkyl) isocyanurate, wherein the hydroxyalkyl residue comprise 1 to 8 C-atoms and may be linear, branched and/or cyclic, in particular 1 to 6 C-atoms, preferably 1 to 4 C-atoms, preferably 1 to 3 C-atoms, particularly preferred is hydroxyethyl, and
(b) 5 to 35% by weight at least one di-functional acrylate having a bivalent alicyclic group and/or di-functional methacrylate having a bivalent alicyclic group, and
(c) 20 to 50% by weight, in particular 30 to 50% by weight at least one disubstituted 4,4'-di(oxabenzol) dialkyl methane of formula I with $R^1$, $R^2$, $R^5$ and $R^6$ each independently selected from H or C1 to C4-alkyl, and with $R^3$ and $R^4$ each independently bivalent C1 to C4-alkylene, with n=0 to 6 and m=0 to 6, and optionally
(d) 20 to 40% by weight at least one at least di-functional urethane acrylate and/or di-functional urethane methacrylate,
(e) 5 to 20% by weight, in particular 5 to 15% by weight, at least one mono-functional acrylate having an alicyclic group and/or mono-functional methacrylate having an alicyclic group, and optionally
(f) 1 to 20% by weight at least one mono-, tri-, tetra- or multi-functional monomer, in particular acrylic ester and/or methacrylic ester of polyethers selected from dimethacrylic esters of polyethers, tri-, tetra- or multi-functional methacrylic esters of polyethers, diacrylic esters of polyethers, tri-, tetra- and/or multi-functional acrylic esters of polyethers,
(ii) 0.01 to 5% by weight of the at least one further component comprising at least one photo-initiator for the UV- and/or vis spectral region or a photo-initiator system for the UV and/or vis spectral region, and optionally at least one stabiliser for the UV and/or Vis spectral region, and optionally at least one pigment and/or dye, as well as further usual additives, wherein the total composition amounts to 100% by weight.

Particularly preferred photo-initiators comprise alpha-hydroxyphenyl ketone, benzil dimethyl ketal or 2,4,6-trimethyl benzoyl diphenyl phosphine oxide, phenyl-bis(2,4,6-trimethylbenzoyl) phosphine oxide, 2,4,6-trimethyl benzoyl phenyl phosphinic acid ethyl ester, and mixtures of at least two of the photo-initiators, phenyl phosphine oxide combinations, bisacryl phosphine oxides (BAPO).

Typical stabilisers comprise 2,6-di-tert.-butyl-4-methyl phenol (BHT) or hydroquinone monomethyl ether (MEHQ), 2-hydroxy-4-methoxybenzophenone, HALS (hindered amine light stabilisers), benzotriazole ultraviolet absorbers (UVAs) and hydroxyphenyl triazines (HPT).

According to a further preferred embodiment, the composition may comprise:
(ii) 0.01 to 2% by weight photo-initiators for the UV and/or Vis spectral region or a photo-initiator system for the UV and/or vis spectral region, and 0.01 to 2% by weight stabiliser, and optionally (g) 0 to 10% by weight, in particular 0.01 to 7.5% by weight inorganic fillers comprising inorganic oxides or inorganic mixed oxides and/or dental glasses, in particular zirconium dioxide, mixed oxides of zirconium oxide and silicon dioxide, silicon dioxide, wherein the total composition amounts to 100% by weight.

Likewise, a subject matter of the invention are compositions, comprising fillers having primary particle sizes of the inorganic fillers, optionally being present as agglomerated and/or aggregated primary particles, of in average having a particle diameter of circa 3 to 70 nm, in particular from 10 bis 50 nm. Alternatively or additionally, usual fillers having particle sizes of 0.4 to 10 μm may be used in the composition.

Furthermore, a subject matter of the invention is a polymerised composition as well as an appropriate 3D moulded body, as well as also the dental models, splints, orthodontic appliances and prosthetic moulded parts or blanks mentioned below, wherein the polymerised composition alternatively or cumulatively has i) a) a flexural strength of greater than or equal to 75 MPa (following DIN EN ISO 20795-2), and/or b) an E-modulus of greater than or equal to 2000 MPa (following DIN EN ISO 20795-2), and/or
ii) a) a flexural strength of greater than or equal to 70 MPa (following DIN EN ISO 20795-2), in particular measured in water at 37° C., and/or b) an E-modulus of greater than or equal to 2000 MPa (following DIN EN ISO 20795-2), in particular measured in water at 37° C., and/or iii) a) a flexural strength of greater than or equal to 50 MPa (following DIN EN ISO 20795-2), in particular measured in water at 45° C., and/or b) an E-modulus of greater than or equal to 1500 MPa (following DIN EN ISO 20795-2), in particular measured in water at 45° C., and/or iv) a) a flexural strength of greater than or equal to 40 MPa (following DIN EN ISO 20795-2), in particular measured in water at 55° C., and/or b) an E-modulus of greater than or equal to 900 MPa (following DIN EN ISO 20795-2), in particular measured in water at 55° C., in particular being obtainable by irradiation of a polymerisable composition.

In this context, it is particularly preferred for the polymerised composition to have a shrinkage of less than 7%, preferably a shrinkage of less than or equal to 6.8%, preferred less than or equal to 6.5%, particularly preferably less than or equal to 6.0% (determined according to Watts, Dent. Mater 7: 281-286, Okt. 1991, also referred to as Bonded Disc-Method, at ambient room temperature, Translux Energy, 60 s lighting).

Furthermore, a subject matter of the invention is a blank in the form of a three-dimensional moulded body of a polymerised composition suitable for producing dental prosthetic parts, orthopaedic appliances or dental pre-forms, wherein the blank has a.1) a flexural strength of greater than or equal to 75 MPa (following DIN EN ISO 20795-2) and/or b.1) an E-modulus of greater than or equal to 2000 MPa (following DIN EN ISO 20795-2), and optionally a.2) a flexural strength of greater than or equal to 50 MPa (following DIN EN ISO 20795-2), in particular measured in water at 45° C., and/or b.2) an E-modulus of greater than or equal to 1500 MPa (following DIN EN ISO 20795-2), in particular measured in water at 45° C., and optionally iv) a) a flexural strength of greater than or equal to 40 MPa (following DIN EN ISO 20795-2), in particular measured in water at 55° C., and/or b) an E-modulus of greater than or equal to 900 MPa (following DIN EN ISO 20795-2), in particular measured in water at 55° C.

Also a subject matter of the invention is the use of a composition for producing anatomical models, anatomical table-top models, anatomical models for replacement of the dental plaster model of the dentition, prosthetic parts, dental prosthetic parts, orthopaedic appliances, aligners, dental splints, or dental pre-forms, as well as the use of a composition according to the invention in a rapid prototyping or in a rapid manufacturing or rapid tooling method. Preferred is a radiation-curing of the composition by means of laser beams, LED light sources or DLP projectors.

Furthermore, a subject matter of the invention is the use of a composition for producing dental prosthetic parts comprising prosthesis base or parts thereof, artificial teeth, dental arch having at least two to 16 artificial teeth being interdentally connected in an integral manner, crowns, provisional crowns, total prostheses, total crowns, splints for orthodontic corrections (similar to Invisalign), dental bridges, abutments, suprastructures, dental bars, inlays, onlays, orthopaedic appliances, such as occlusal splints, dental pre-forms of artificial teeth, surgical guides for implantology, mouthguards, and/or implants.

Presently, dental products are in particular understood to mean dental products being producible from polymerisable compositions, such as e.g. not exhaustive total protheses, provisional crowns and bridges, inlays, onlays, total crowns, occlusal splints, surgical guides for implantology, splints for orthodontic corrections (similar to Invisalign), mouthguards, artificial teeth.

In order to meet high aesthetic requirements, compositions usable in dental field for producing definitive dental restorations, such as e.g. work models, orthodontic models, surgical guides, temporary protheses as well as splints, must have a high degree of transparency. This transparency is usually achieved by optimal adaption of the refractive indices of the fillers and the polymer matrix. However, due to various physical and chemical boundary conditions, very narrow limits are set for the selection of both fillers and monomers.

According to a further alternative embodiment, polymerised compositions or blanks are obtainable, in particular radiation-cured compositions, in particular UV-Vis-cured compositions, preferably being additionally radiation-cured from all sides, having the following properties with regard to their flexural strength and/or E-modulus following DIN EN USO 20795-2. Additional radiation-curing from all sides is understood to mean post-tempering in 3D light furnace for example.

In this context, the following methods—rapid prototyping or rapid manufacturing, a method for producing work pieces, such as a dental prosthetic part, or rapid tooling, a method for producing tools—each comprise stereolithography methods and DLP methods. Optionally, post-tempering with UV, Vis or UV-Vis light may be carried out in the afore-mentioned methods after curing of the polymerisable composition. Preferably, post-tempering of the polymerised composition or of the dental prosthetic parts, of the orthopaedic appliances or dental pre-forms or blanks is carried out concurrently from at least three sides, preferably from five to six sides, as it is possible in a light furnace. Alternatively, the polymerised composition may be tempered additionally or alternatively.

Colour pigments may additionally be added to the composition to adjust the colour. In addition, red fibres may be added to the composition to imitate blood vessels of the gingiva. Suitable colour pigments are for example: PV pigment red—CAS 4948-15-6, pigment blue 220943—CAS 68186-87-8, pigment black 100—CAS 68186-91-4, Kronos 2220—CAS 13463-67-7 and light yellow 3R—CAS 68186-90-3.

Layer thicknesses in the range of 5 μm, in particular from 25 μm to 250 μm, per curing layer may be achieved in the polymerised compositions. The printed layers are particularly preferably at 30 μm, 50 μm, 70 μm, 100 μm, 120 μm and 170 μm.

High transparency may be achieved by optimal selection of the recipe components in respect of their refractive indices.

Benzoin alkyl ethers or esters, benzil monoketales, acylphosphine oxides or aliphatic and aromatic 1,2-diketo compounds, such as for example 2,2-diethoxyacetophenone, 9,10-phenanthrene quinone, diacetyl, furil, anisil, 4,4'-dichlorobenzil and 4,4'-dialkoxybenzil or camphorquinone, are conceivable as photoinitiators for example. The photoinitiators are preferably used together with a reducing agent. Examples for reducing agents include amines such as aliphatic or aromatic tertiary amines, for example N,N-dimethyl-p-toluidine or triethanol amine, cyan ethyl methyl aniline, triethyl amine, N,N-dimethyl aniline, N-methyl diphenyl amine, N,N-dimethyl-sym.-xylidine, N,N-3,5-tetramethyl aniline and 4-dimethyl aminobenzoic acid ethyl ester or organic phosphites. Usual photoinitiator systems are e.g. camphor quinone plus ethyl-4-(N,N-dimethylamino)

benzoate, 2-(ethylhexyl)-4-(N,N-dimethylamino)benzoate or N,N-dimethyl aminoethyl methacrylate.

2,4,6-trimethyl benzoyl diphenyl phosphine oxide is particularly suitable as initiator for polymerisation initiated by UV light. UV photo-initiators may be used alone or in conjunction with an initiator for visible light.

Particularly preferred photo-initiators and/or initiator systems comprise a) at least one radical photo-initiator, in particular at least one peroxide and/or azo compound, in particular LPO: dilauroyl peroxide, BPO: dibenzoyl peroxide, t-BPEH: tert.-butylper-2-ethyl hexanoate, AIBN: 2,2'-azobis-(isobutyronitrile), DTBP: di-tert.-butyl peroxide, or an alpha-hydroxy ketone, camphorquinone, acyl phosphine oxide. Optionally, stabilisers may be added additionally and optionally b) at least one co-initiator such as an amine, usually a tert-amine, in particular at least one aromatic amine, such as N,N-dimethyl-p-toluidine, N,N-dihydroxyethyl-p-toluidine and/or p-dibenzyl aminobenzoic acid diethyl ester.

Particularly preferred photo-initiators comprise alpha-hydroxyphenyl ketone, benzil dimethyl ketal or 2,4,6-trimethyl benzoyl diphenyl phosphine oxide, phenyl-bis(2,4,6-trimethylbenzoyl) phosphine oxide, 2,4,6-trimethyl benzoyl phenyl phosphinic acid ethyl ester, and mixtures of at least two of the photo-initiators, phenyl phosphine oxide combinations, bisacryl phosphine oxides (BAPO).

Typical stabilisers comprise 2,6-di-tert.-butyl-4-methyl phenol (BHT) or hydroquinone monomethyl ether (MEHQ), 2-hydroxy-4-methoxybenzophenone, HALS (hindered amine light stabilisers), benzotriazole ultraviolet absorbers (UVAs) and hydroxyphenyl triazines (HPT).

The invention is explained in more detail by the following examples without limiting the invention to these exemplary embodiments.

The composition according to the invention may be used to print work pieces, blanks or three-dimensional moulded bodies having very good geometrical precision/resolution. The moulded bodies according to the invention have very good mechanical properties even at elevated temperatures. Furthermore, good colour stability can be observed in the work pieces.

EXEMPLARY EMBODIMENTS

General example of production: the initiators are pre-dissolved in TCD acrylate or TCD diacrylate. Subsequently, the other monomers are added and the mixture is homogenised. Pigment concentrates or pigments may be added, the composition is then preferably homogenised. The composition produced is processable with a 3D printer. It is to be noted that the light-sensitive initiators may react to an undesired polymerisation in connection with the ambient light (the composition is preferably transferred into the pressure bath under appropriate measures). Lighting is carried out at 385-405 nm and post-curing or post-tempering, respectively, is carried out e.g. with a laboratory light device HiLite Power 3D.

The mixture produced is used to print test specimens according to ISO 20795-2 (50 µm) for the following tests on a 3D precision printer having the wavelength 405 nm (Cara Print 4.0). The test specimens were washed up with isopropanol after the printing process and subjected to a post-tempering process. The said was carried out by lighting on both sides in a laboratory light device HiLite Power 3D, 200 W (Kulzer GmbH) for 3 to 5 min respectively or as specified by the manufacturer. Properties of the mixture according to the invention for modelling materials, tested according to DIN EN ISO 20795-2 or following the norm, respectively.

TABLE 1a

Thermostability of compositions according to the invention

| | | | Example 1 | Example 2 | Example 3 |
|---|---|---|---|---|---|
| Thermostability Mechanics followed (ISO 20795-2) | Calculated TG | | 135 | 186 | 201 |
| Storage | Measurement | | | | |
| Storage dry | Testing dry | Flexural strenght in [MPa] | 84.2 | 90.6 | 95.3 |
| | | E-modulus in [MPa] | 2615 | 2785 | 2859 |
| Storage dry | in water (37° C.) | Flexural strenght in [MPa] | 81.2 | 71 | 79.4 |
| | | E-modulus in [MPa] | 2185 | 2316 | 2412 |
| Storage dry | in water (45° C.) | Flexural strenght in [MPa] | 58.2 | 66.4 | 75.7 |
| | | E-modulus in [MPa] | 1559 | 1889 | 1993 |
| Storage dry | in water (55° C.) | Flexural strenght in [MPa] | 44.9 | 59.3 | 60.2 |
| | | E-modulus in [MPa] | 940 | 1485 | 1582 |
| Shrinkage according to Watts | | [%] | 5.5 | 6.41 | 6.76 |
| Viscosity [m · Pas] | | | 1390 | 1560 | 2224 |

TABLE 1b

Compositions according to the invention

| Monomeres | TG (homopolymer) for w1/Tg$_{(1)}$ to wn/Tg$_{(n)}$ | Example 1 Amount in % by weight | Example 2 Amount in % by weight | Example 3 Amount in % by weight |
|---|---|---|---|---|
| aliphatic urethane dimethacrylate | 148 | 27.7 | | 32.5 |
| ethoxylated (2) bisphenol-A dimethacrylate | 105 | 40 | 32.5 | |
| tris(2-hydro)ryethyl) isocyanurate triacrylate | 270 | 10 | 32.5 | 32.5 |
| (Octahydro-4,7-metano-1H-indenyl) methylacrylate | 35 | 10 | | |
| tricyclodecane dimethanol diacrylate | 185 | 10 | 32.5 | 32.5 |

TABLE 2

Composition according to the invention

| | Mixture 4 | MW | % by weight |
|---|---|---|---|
| Stabiliser | 2-hydroxy-4-methoxybenzophenone | | 0.01-1.00 |
| Initiator | phenyl-bis(2,4,6-trimethylbenzoyl) phosphine oxide | | 0.01-3.00 |
| Monomers | urethane dimethacrylate (oligomer) | 700 | 10-30.00 |
| | tris-(2-hydroxyethyl) isocyanurate triacrylate | 423.38 | 10-30 |
| | ethoxylated bisphenol-A dimethacrylate | av. 1700 | 20-50 |
| | (Octahydro-4,7-methano-1H-indenyl) methylacrylate | 220.31 | 10-30 |
| | tricyclodecane dimethanol diacrylate | 304.38 | 10-30 |
| Pigments | Kronos 2056 sil. | | 0.01-2.0 |
| | Light Yellow 3R | | 0.01-1.00 |
| | Pigment Black 100 | | 0.01-1.00 |
| | Red 100 | | 0.01-1.00 |
| Total: | | | 100.00 |

TABLE 3

Thermostability compositions of third parties
Thermostability

| Storage | Testing | | Mechanics following ISO 20795-2 | Dreve Foto-dent | Detax Free Print | B9 Creations B9R-5 |
|---|---|---|---|---|---|---|
| Storage dry | dry | Flexural strength in [MPa] | 73.2 | 74.9 | 46.9 | |
| | | E-modulus in [MPa] | 1991 | 1697 | 983 | |
| Storage dry | in water (37 °C.) | Flexural strength in [MPa] | 65.8 | 35 | 11.1 | |
| | | E-modulus in [MPa] | 1594 | 557 | F max-18 | |
| Storage dry | in water (45 °C.) | Flexural strength in [MPa] | 54 | not possible | not possible | |
| | | E-modulus in [MPa] | 1288 | | | |
| Storage dry | in water (55 °C.) | Flexural strength in [MPa] | 40.9 | not possible | not possible | |
| | | E-modulus in [MPa] | 914 | | | |
| Shrinkage according to Watts | | [%] | 5.83 | 7.7 | 7.2 | |

The invention claimed is:

1. Polymerisable radiation-curable composition comprising
    (i) monomers and
    (ii) and least one further component,
    wherein
    (i) the monomers comprise
    (a.1) at least one triacrylate derived from 1,3,5-tris(ω-hydroxyalkyl) isocyanurate, wherein the hydroxyalkyl residue each independently comprises 1 to 8 C-atoms, and
    (a.2) at least one di-functional monomer, not being a urethane acrylate or urethane methacrylate, which comprises (b) and/or (c),
        (b) di-functional acrylates having a bivalent alicyclic group and/or di-functional methacrylates having a bivalent alicyclic group,
        (c) at least one disubstituted 4,4'-di(oxabenzol) dialkyl methane of formula I

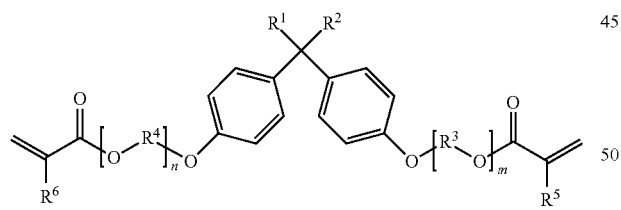

with $R^1$, $R^2$, $R^5$ and $R^6$ each independently selected from H or C1 to C4-alkyl, and with $R^3$ and $R^4$ each independently bivalent C1 to C4-alkylene, with n=0 to 6 and m=0 to 6, and optionally
    (d) at least one at least di-functional urethane (meth) acrylate,
    (e) at least one mono-functional acrylate having an alicyclic group and/or mono-functional methacrylate having an alicyclic group, and
    (ii) the at least one further component comprises
        at least one photo-initiator for the UV- and/or Vis spectral region or a photo-initiator system for the UV- and/or Vis spectral region, and optionally a stabiliser.

2. Composition according to claim 1, wherein the viscosity of the composition at ambient room temperature (approx. 20° C. to 23° C.) is less than or equal to 3000 m·Pas.

3. Composition according to claim 1, wherein
    (a.1) the at least one triacrylate derived from 1,3,5-tris (ω-hydroxyalkyl) isocyanurate comprises 1,3,5-tris(2-hydroxyethyl) isocyanurate triacrylate, 1,3,5-tris(2-hydroxymethyl) isocyanurate triacrylate, 1,3,5-tris(2-hydroxyethyl) isocyanurate trimethacrylate, 1,3,5-tris (2-hydroxymethyl) isocyanurate trimethacrylate or mixtures containing at least two of the monomers.

4. Composition according to claim 1, wherein the at least one di-functional monomer, not being a urethane (meth) acrylate, is selected from (b) di-functional acrylates having a bivalent alicyclic group and di-functional methacrylates having a bivalent alicyclic group.

5. Composition according to claim 1, wherein (b) is selected from tricyclodecane dimethanol diacrylate (TCDDA), tricyclodecane dimethanol dimethacrylate, tricyclodecane diethanol diacrylate, tricyclodecane diethanol dimethacrylate and/or mixtures thereof.

6. Composition according to claim 1, wherein the (a.2) at least one di-functional monomer, not being a urethane (methacrylate), comprises (c) at least one disubstituted 4,4'-di(oxabenzol) dialkyl methane of formula I

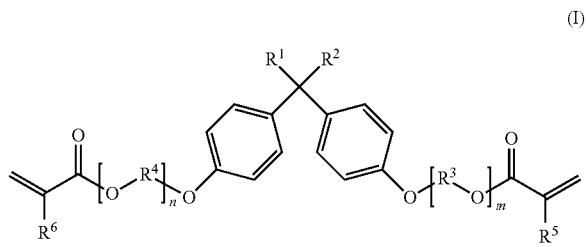

with $R^1$ and $R^2$ each methyl, and $R^5$ and $R^6$ the same and selected from H, methyl and ethyl, and with $R^3$ and $R^4$ each independently bivalent ethylene or propylene with n=1 to 6 as well as mixtures thereof.

7. Composition according to claim 1, wherein the
    (d) at least one di-functional urethane acrylate or urethane methacrylate is selected from di-functional urethane acrylates having a bivalent alkylene group and urethane methacrylates having a bivalent alkylene group, and/or
    (e) at least one mono-functional acrylate having an alicyclic group and/or mono-functional methacrylate having an alicyclic group is selected from (octahydro-4,7-methano-1H-indenyl) methanol acrylate, (octahydro-4,7-methano-1H-indenyl) methanol methacrylate, (octahydro-4,7-methano-1H-indenyl) ethanol acrylate and (octahydro-4,7-methano-1H-indenyl) ethanol methacrylate and mixtures containing them, and optionally
    (f) at least one mono-, tri-, tetra- or multi-functional monomer.

8. Composition according to claim 1, comprising (i) monomers comprising
    (a) 5 to 45% by weight at least one triacrylate derived from 1,3,5-tris(ω-hydroxyalkyl) isocyanurate, wherein the hydroxyalkyl residue comprises 1 to 8 C-atoms, and
    (b) 5 to 45% by weight at least one di-functional acrylate having a bivalent alicyclic group and/or di-functional methacrylate having a bivalent alicyclic group, and (c) 0 to 60% by weight at least one disubstituted 4,4'-di (oxabenzol) dialkyl methane of formula I

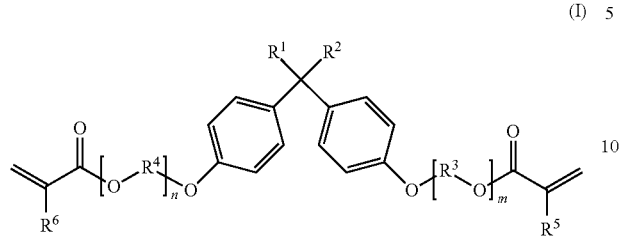

with $R^1$, $R^2$, $R^5$ and $R^6$ each independently selected from H or C1 to C4-alkyl,
and with $R^3$ and $R^4$ each bivalent C1 to C4-alkylene, with n=0 to 6 and m=0 to 6, and optionally
(d) 0 to 60% by weight at least one at least di-functional urethane acrylate and/or di-functional urethane methacrylate,
(e) 0 to 20% by weight at least one mono-functional acrylate having an alicyclic group and/or mono-functional methacrylate having an alicyclic group, and
(ii) 0.01% by weight to 5% by weight of the at least one further component comprising
at least one photo-initiator for the UV and/or Vis spectral region or a photo-initiator system for the UV and/or Vis spectral region, and optionally at least one stabiliser for the UV- and/or Vis spectral region, and optionally at least one pigment and/or dye as well as further usual additives,
wherein the total composition amounts to 100% by weight.

9. Composition according to claim 8, comprising (i) monomers comprising
(a) 5 to 35% by weight at least one triacrylate derived from 1,3,5-tris(ω-hydroxyalkyl) isocyanurate, wherein the hydroxyalkyl residue comprises 1 to 8 C-atoms and may be linear, branched and/or cyclic, and
(b) 5 to 35% by weight at least one di-functional acrylate having a bivalent alicyclic group and/or di-functional methacrylate having a bivalent alicyclic group, and
(c) 20 to 50% by weight at least one disubstituted 4,4'-di(oxabenzol) dialkyl methane of formula I

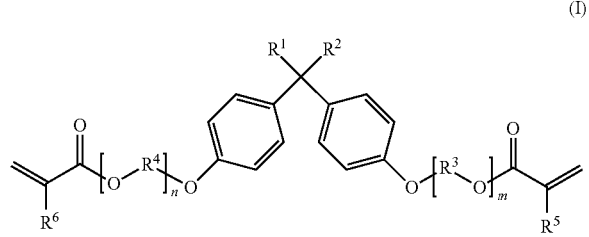

with $R^1$, $R^2$, $R^5$ and $R^6$ each independently selected from H or C1 to C4-alkyl,
and with $R^3$ and $R^4$ each bivalent C1 to C4-alkylene, with n=0 to 6 and m=0 to 6, and optionally
(d) 20 to 40% by weight at least one at least di-functional urethane acrylate and/or di-functional urethane methacrylate,
(e) 5 to 20% by weight at least one mono-functional acrylate having an alicyclic group and/or mono-functional methacrylate having an alicyclic group, and optionally
(f) 1 to 20% by weight at least one mono-, tri-, tetra- or multi-functional monomer,
(ii) 0.01 to 5% by weight of the at least one further component comprising
at least one photo-initiator for the UV and/or Vis spectral region or a photo-initiator system for the UV- and/or Vis spectral region, and optionally at least one stabiliser for the UV- and/or Vis spectral region, and optionally at least one pigment and/or dye as well as further usual additives,
wherein the total composition amounts to 100% by weight.

10. Polymerised composition according to claim 1, wherein the polymerised composition has, alternatively or cumulatively,
i) a) a flexural strength of greater than or equal to 75 MPa (following DIN EN ISO 20795-2), and/or b) an E-modulus of greater than or equal to 2000 MPa (following DIN EN ISO 20795-2), and/or
ii) a) a flexural strength of greater than or equal to 70 MPa (following DIN EN ISO 20795-2), measured in water at 37° C., and/or b) an E-modulus of greater than or equal to 2000 MPa (following DIN EN ISO 20795-2), measured in water at 37° C., and/or
iii) a) a flexural strength of greater than or equal to 50 MPa (following DIN EN ISO 20795-2), measured in water at 45° C., and/or b) an E-modulus of greater than or equal to 1500 MPa (following DIN EN ISO 20795-2), measured in water at 45° C., and/or
iv) a) a flexural strength of greater than or equal to 40 MPa (following DIN EN ISO 20795-2), measured in water at 55° C., and/or b) an E-modulus of greater than or equal to 900 MPa (following DIN EN ISO 20795-2), measured in water at 55° C.

11. Blank in the form of a three-dimensional moulded body of a polymerised composition according to claim 1 for producing dental prosthetic parts, orthopaedic appliances or dental pre-forms, wherein the blank has a.1) a flexural strength of greater than or equal to 75 MPa (following DIN EN ISO 20795-2), and/or b.1) an E-modulus of greater than or equal to 2000 MPa (following DIN EN ISO 20795-2), and optionally
a.2) a flexural strength of greater than or equal to 50 MPa (following DIN EN ISO 20795-2), measured in water at 45° C., and/or b.2) an E-modulus of greater than or equal to 1500 MPa (following DIN EN ISO 20795-2), measured in water at 45° C.

12. Method of using a composition according to claim 1 for producing anatomical models, anatomical table-top models, dental working models, dental full models, dental die models, anatomical or dental saw-cut models, situation models, counter-bite models, functional models, Pre-models, repair models, precision models, anatomical models for replacement of the dental plaster model of the dentition, aligners, dental splints, prosthetic pars, dental prosthetic parts, orthopaedic appliances or dental pre-forms, in a rapid prototyping or in a rapid manufacturing or rapid tooling method.

13. Method according to claim 12, wherein the dental prosthetic parts comprise prosthesis base or parts thereof, artificial teeth, dental arch having at least two to 16 artificial teeth being interdentally connected in an integral manner, crowns, provisional crowns, total prostheses, total crowns, splints for orthodontic corrections, dental bridges, abutments, suprastructures, dental bars, inlays, onlays, orthopaedic appliances including occlusal splints, dental pre-forms of artificial teeth, surgical guides for implantology, mouthguards, and/or implants.

\* \* \* \* \*